United States Patent [19]

Mandroian

[11] 4,265,601
[45] May 5, 1981

[54] THREE VALVE PRECISION PUMP APPARATUS WITH HEAD PRESSURE FLOWTHROUGH PROTECTION

[76] Inventor: Harold Mandroian, 2137 Los Amigos, La Canada, Calif. 91011

[21] Appl. No.: 60,955

[22] Filed: Jul. 26, 1979

Related U.S. Application Data

[63] Continuation-in-part of Ser. No. 939,924, Sep. 5, 1978.

[51] Int. Cl.³ .................. F04B 21/02; F04B 17/00; F04B 43/02
[52] U.S. Cl. .................................. 417/379; 417/458; 417/479
[58] Field of Search ............... 417/279, 458, 479, 379, 417/380

[56] References Cited

U.S. PATENT DOCUMENTS

| | | | |
|---|---|---|---|
| 2,228,292 | 1/1941 | Wood | 417/279 |
| 3,045,874 | 7/1962 | Kogan et al. | 417/379 X |
| 3,232,497 | 2/1966 | Schoeppach | 417/279 X |
| 3,250,224 | 5/1966 | Phillips et al. | 417/479 |
| 3,368,495 | 2/1968 | Turner | 417/380 |
| 4,124,008 | 11/1978 | Fujikawa | 417/380 |

Primary Examiner—Leonard E. Smith

[57] ABSTRACT

A pumping apparatus for moving a pumped fluid from a reservoir to a destination in response to variations in the pressure of a pumping fluid includes a pump housing; a pumping chamber; an input passageway; an exit passageway; and a passageway network between the input passageway and the exit passageway. A diaphragm divides the pumping chamber into first and second volumes for respectively receiving the pumped and the pumping fluids. Apparatus is provided for intermittantly varying the pressure of the pumping fluid. A first diaphragm valve responsive to variations in the pressure of the pumped fluid is positioned between the input passageway and the passageway network. A second valve also responsive to variations in the pressure of the pumped fluid is positioned in the passageway network for being opened when the first valve is closed and visa versa. A third valve is positioned between the exit passageway and the second valve in the passageway network to prevent pumped fluid flowthrough caused by a pressure head at the input or exit ports.

8 Claims, 4 Drawing Figures

THREE VALVE PRECISION PUMP APPARATUS WITH HEAD PRESSURE FLOWTHROUGH PROTECTION

This is a continuation-in-part application of application Ser. No. 939,924 filed Sept. 5, 1978.

BACKGROUND OF THE INVENTION

The present invention relates to pumps and pumping systems and, in particular, to pumps having accurate pumping rates and pumping volumes.

Fluid pumps are typically based upon the use of a rotating or reciprocating device such as an impeller which is bearing mounted and driven by some motive means such as an electric motor. Such mechanical pumps, while reasonably efficient, uniformly suffer from the problems of wear of the moving parts as well as significant levels of audible noise. In order to solve the problems of wear, a pump having essentially no moving parts was developed and is disclosed in my U.S. Pat. No. 3,898,017, issued Aug. 5, 1975. In that patent, a heater ribbon is placed in a chamber containing the pumped fluid. This allows the fluid being pumped to come in contact with the heating ribbon. Such direct contact may not be desirable in some medical applications where it is desired to pump fluids having a delicate or fragile structure or which are subject to breakdown in the presence of high temperature. In addition, it is frequently necessary to keep the pumped fluid separated from a reusable heater to maintain a sterile environment for the pumped fluid.

The present invention, in meeting these problems, provides a pump which incorporates a movable diaphragm for separating the fluid being pumped from the heating ribbon or element so that the pumped fluid is not affected by the heat from the heating element, and further will not be contaminated by contaminants which may exist around the heating element or in the chamber in which the heating element is placed. The pumping of the pumped fluid thus occurs in response to the expansion and contraction of a pumping fluid which is different from the pumped fluid and which preferably has a high expansion ratio and low specific heat. Although such a pumping fluid is preferably a gas, it may be a liquid or may be a fluid which changes state, for example, from a liquid to a gas upon heating and then back to a liquid when the heater is cool. In addition, the present invention, in using a diaphragm in a pumping chamber with a fixed volume, provides a means of very accurately defining the pumped volume of the fluid. This occurs by causing the diaphragm to be displaced by the pumping fluid upon its expansion against the sides of the pumping chamber thereby expelling all of the pumped fluid in the chamber. Thus, the volume of the fluid pumped on each pumping cycle is accurately defined by the volume of the pumping chamber. The present invention also provides a means for easily adjusting the flow rate, as well as providing increased fluid pressures. The pump of the present invention may be a positive displacement type pump or may incorporate a variable displacement feature by controlling the amount by which the pumping fluid expands due to heating by the heater. Finally, the present pump invention is free of audible noise. In U.S. Pat. No. 2,884,866 issued May 5, 1959, a pumping mechanism is disclosed which attempted to provide accurate pumping volumes. However, in that patent, no fixed volume chamber is provided to define an accurate per cycle pumped volume. Finally, the interior of the sock-type flexible member defining the cycle pumping volume can not be accurately evacuated on each cycle thus resulting in additional inaccuracy in pumping volume and rate. It will be appreciated that in many I.V. pumping applications, pumping accuracy unachievable by the above-cited patent but easily obtained by the present invention, is a necessity.

Various other apparatus using pistons (which have undesirable friction and sealing characteristics), manual or independent valve operation, single-cycle rather than continuous multiple-cycle operation, intermingling of the pumped and the pumping fluid, no volume-defining pumping chamber, and various other disadvantages are described in various of the U.S. Pat. Nos. 2,,389,067; 2,576,282; 2,867,224; 2,884,866; 3,045,874; 3,074,596; 3,099,222; 3,149,754; 3,604,821; 3,645,649; 3,859,012; 3,901,629; and Re. 27,740.

SUMMARY OF THE INVENTION

The present invention comprises a pumping system having a pump apparatus coupled between a reservoir and a destination for pumping fluid from the reservoir along a flow path in which a pump chamber is placed. A diaphragm bifurcates the pump chamber into a first chamber volume for receiving the pumped fluid and a second chamber volume for containing a pumping fluid. A heater apparatus is coupled to the pump apparatus and comprises a heating chamber for containing a quantity of the pumping fluid. The heating chamber is coupled by a passageway to the second chamber volume of the pump chamber. An electrical heater is also provided in the pumping chamber for heting the quantity of pumping fluid. Finally, a heater control means is coupled to the electrical heater and provides intermittent electrical pulses for energizing the heater and thereby heating the pumping fluid to cause the pumping fluid to expand which in turn causes the diaphragm to expand forcing the pumped fluid from the first chamber volume of the pump chamber.

Additional features of the present invention may be provided and include one or more potentiometers or other control devices known in the art which may be incorporated in the heater control circuitry to allow the pulse repetition rate or the pulse duration of the electrical pulses energizing the electrical heater or both to be varied.

It will also be appreciated that the pump apparatus may be of either the positive-displacement or the variable-displacement type. In addition, a feedback control loop may be provided by incorporating, for example, a flow rate sensor in the hydraulic circuit of the pumping system. The sensor generates a signal proportional to the flow rate which may be fed back and utilized to vary the amplitude, period, or duration of the electrical pulses provided to the heater to thereby vary the amount of heating and, thus, expansion of the pumping fluid in the second chamber volume. Such a feedback control loop is particularly useful in a variable displacement pumping embodiment.

A third valve is also provided in the exit passageway to be actuated in response to a head pressure to prevent flow through when, for example, the first and second valves are opened in response to the head pressure.

Of course, it will be appreciated that many other variations and modifications of the present invention and its various components are possible such as replacing the valves in the input and exit passageways with an egress restriction means or ingress restriction means to induce flow in a single direction by providing less resistance to flow in one direction than in the other. Such a modification is disclosed in my U.S. Pat. No. 3,898,017. Also it will be appreciated that the pumping fluid utilized in the heating chamber may be air or a gas such as argon or helium which have greater thermal expansion per unit of heat energy than air.

BRIEF DESCRIPTION OF THE DRAWINGS

The invention will be better understood from the detailed description below taken in conjunction with the drawings wherein like reference characters refer to like parts througout and in which.

DETAILED DESCRIPTION OF THE PREFERRED EMBODIMENT

Figure 1:
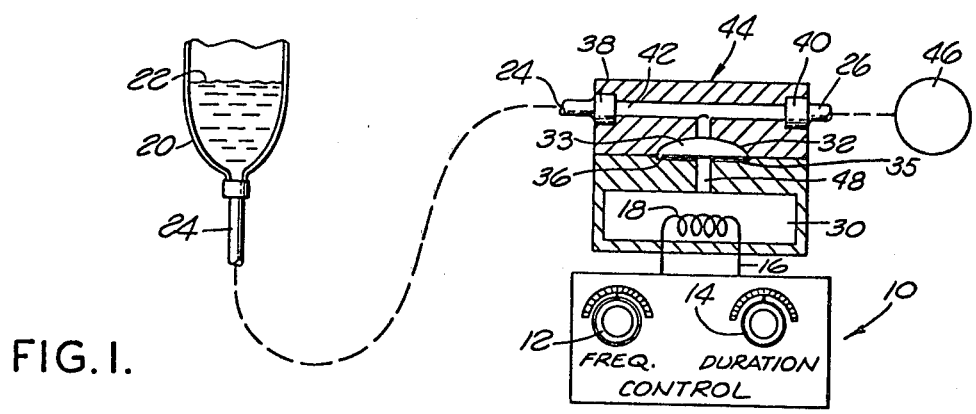
FIG. 1 is a simplified representation showing a cross-section of a pump apparatus and the associated control unit for varying the frequency and pulse width of the signal applied to the heater.

The pumping system of the present invention may be generally understood by reference to FIG. 1 which shows a pump apparatus 44 electrically coupled to a control means 10 for pumping fluid 22 from a container 20 to a destination 46. In the preferred application of the various embodiments of the present invention, the pump introduces a fluid or drug from a pouch or other container into the blood stream of a patient who would typically be the destination for the fluid (hereinafter the pumped fluid).

More specifically, the pump apparatus 44 has a pump chamber 32 bifurcated by a membrance or diaphragm 36 into a first chamber volume 33 for receiving pumped fluid and a second chamber volume 35 for containing the pumping fluid. An enclosed heating chamber 30, which contains a pumping fluid such as air or some other gas is then connected by a passageway to the second chamber volume 35. The diaphragm 36 moves back and forth within the pump chamber 32 in response to increases and decreases in the gas pressure in the heating chamber 30.

Fluid is introduced into the pump apparatus from the reservoir 20 along an input passageway 24. A one-way valve 38 is interposed between the input passageway 24 and an internal passageway 42 to assure that the pumped fluid 22 will not be pumped back into the input passageway 24. Connected between the internal passageway 42 and an exit passageway 26 is a second one-way valve 40 which prevents pumped fluid expelled from the pump apparatus 44 from returning to the internal passageway 42.

In operation, once all of the air has been bled from the input passageway 24, the pumped fluid portion 33 of the pump chamber 32, and the internal passageway 42, an increase in pumping fluid pressure in the heating chamber 30 causes the diaphragm 36 to be displaced in the direction of the first chamber volume 33 of the pump chamber 32 thereby decreasing the volume of the first chamber volume 33 forcing fluid out into the internal passageway 42. Because the valve 38 prevents the pumped fluid from flowing back into the input passageway 24, the pumped fluid is forced from the internal passageway 42 through the valve 40 into the exit passageway 26.

When the pumping fluid pressure in the heating chamber 30 again decreases, for example, when the heater is de-energized, the diaphragm 36 contracts toward the chamber 30 causing a volume increase in the first chamber volume 33 causing pumped fluid to flow through the valve 38 into the internal passageway 42, and into the first chamber volume 33. No pumped fluid enters through the valve 40 because the fluid pressure in the passageway 42 causes the valve 40 to close.

Although various methods may be utilized to increase and decrease the pumping fluid pressure in the heating chamber 30 to achieve the pumping action required, the preferred method is to intermittently or periodically heat the pumping fluid in the heating chamber 30 by periodically applying an electrical current through a ribbon heater 18 which is connected by leads 16 to the control unit 10. The periodic pulses of electricity through the heater ribbon 18 cause the expansion and contraction of the pumping fluid in the heating chamber 30 necessary to periodically displace the diaphragm 36. Numerous circuits are available which provide periodic power pulses. For example, the control unit 10 may be a power circuit such as that described in my U.S. Pat. No. 3,898,017, issued Aug. 5, 1975, or may be one of the various circuit arrangements disclosed in literature provided by National Semiconductor Corporation in conjunction with their ML-555 timer/pulse generator.

In one embodiment, the circuit described in U.S. Pat. No. 3,898,017 may be modified by providing a potentiometer whose adjustment can change the pulse repetition rate provided to the heating ribbon 18. In such an embodiment, the control unit 10 is provided with a frequency control knob 12 coupled to the potentiometer whereby the frequency of the pulses may be varied. The control unit may also incorporate a variable resistor connected to a control knob 14 for controlling the duration of each pulse. Such modifications in the above described circuits whereby the pulse rate and the pulse width are varied may be provided by electrically controlling an oscillator circuit such as that described in accordance with the circuits shown in various brochures illustrating applications of the No. 555 timer available, for example, from National Semiconductor Corporation. More specifically, both frequency and pulse width can be controlled by applying a voltage to the proper pins on the 555 timer.

Figure 2:
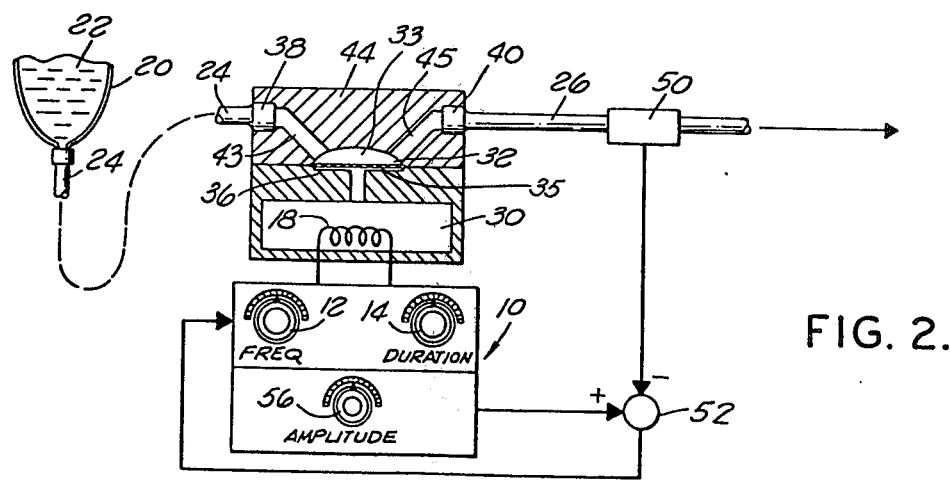
FIG. 2 is a simplified representation of a pump apparatus having separate ports for receiving and expelling pumped fluid in the first chamber volume and incorporating a feedback control loop for varying the amplitude, pulse width, or frequency of the electrical signal to the heater.

Referring to FIG. 2, the present invention is shown incorporating a feedback control loop for controlling the rate at which fluid flows through the exit passageway 26. Such a system is particularly applicable when the pump apparatus 44 is of a variable displacement type where the diaphragm 36 expands only partly into the first chamber volume. Thus, by controlling the amount of heating in the pump chamber 30, the amount of increased pressure pushing against the diaphragm 36 is also controlled and a very precise volume of pumped fluid can be pumped for each cycle of pumping. Further, since the amount of heat energy supplied by the heating ribbon 18 to the pump chamber 30 is related to the amount of power flowing through the heating ribbon 18 supplied by the control unit 10, it can be seen that by controlling the voltage amplitude both the pulse width control 14, or frequency control 12 may be utilized to precisely set the volume and, thus, the flow rate of fluid through the pump. Of course, any other control mechanism to control the pulse width and frequency may be utilized so as to control pumping volume without departing from the invention.

In order to implement such a representative control system, a flow rate sensor 50 may be provided in the exit passageway 26 to sense the rate of flow or the pressure or any other relevant parameter indicative of the pumping volume, rate, or pressure and generate therefrom a substantially constant voltage output proportional to that flow rate, pressure or volume sensed. This voltage value is subtracted from a voltage value, set by an amplitude potentiometer controlled by a knob 56, at a summing junction 52 to provide an error signal output. Of course, it will be appreciated that the sensor 50 and the voltage output from the amplitude potentiometer will be calibrated so that when the flow rate sensed by the sensor 50 equals the values set by the knob 56, then the error will be zero and, thus, the error signal from the summing junction 52 will be zero.

The error signal from the summing junction 52 is then utilized by the pulse rate and duration control circuitry controlled by the frequency control 12 and the duration control 14 to thereby provide feedback control for the amplitude or duration of the pulses utilized to heat the heating ribbon 18. Of course, various other techniques and control configurations may be used for automatically sensing and controlling the amount of energy utilized to heat the gas in the chamber 30. For example, a direct feedback control for the pulse repetition rate or pulse duration without the need of an additional amplitude potentiometer may be incorporated.

Referring particularly to the pump apparatus of FIG. 2 as compared to the pump apparatus of FIG. 1, it will be seen that in FIG. 2 pumped fluid enters the pump chamber via a first passageway 43 and exits via a second passageway 45 each with separate ports in the pump chamber, rather than the single passageway and port configuration of FIG. 1.

Figure 3A:
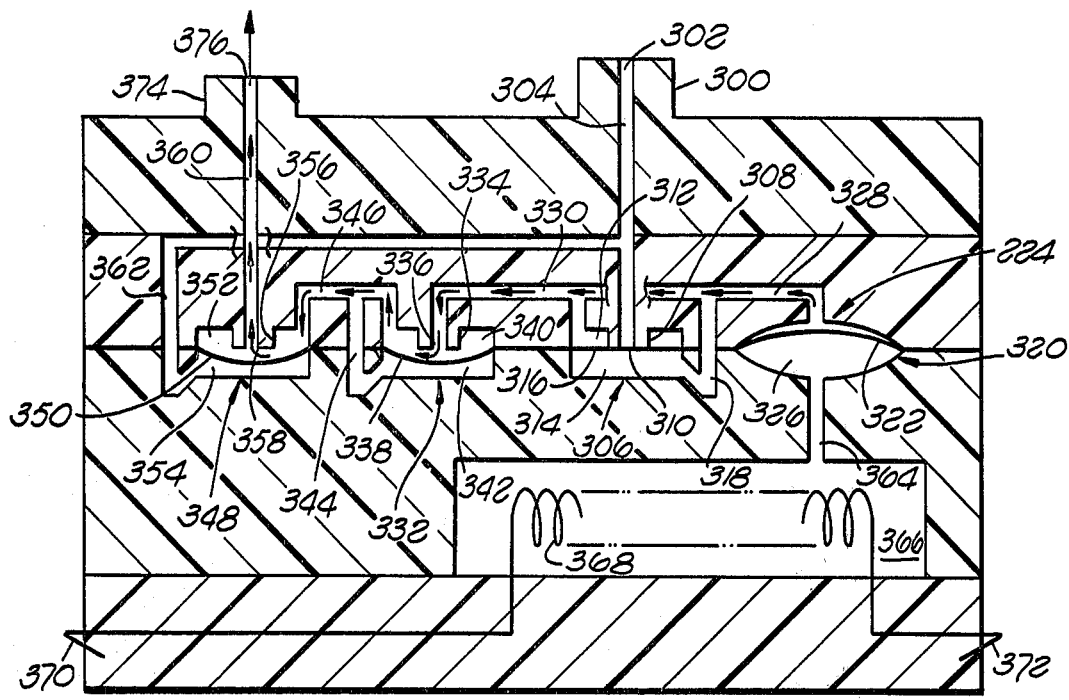
FIGS. 3 and 3B show a cross-sectional view of a pump apparatus in two different operating states incorporating a third flow through prevention valve.
Figure 3B:
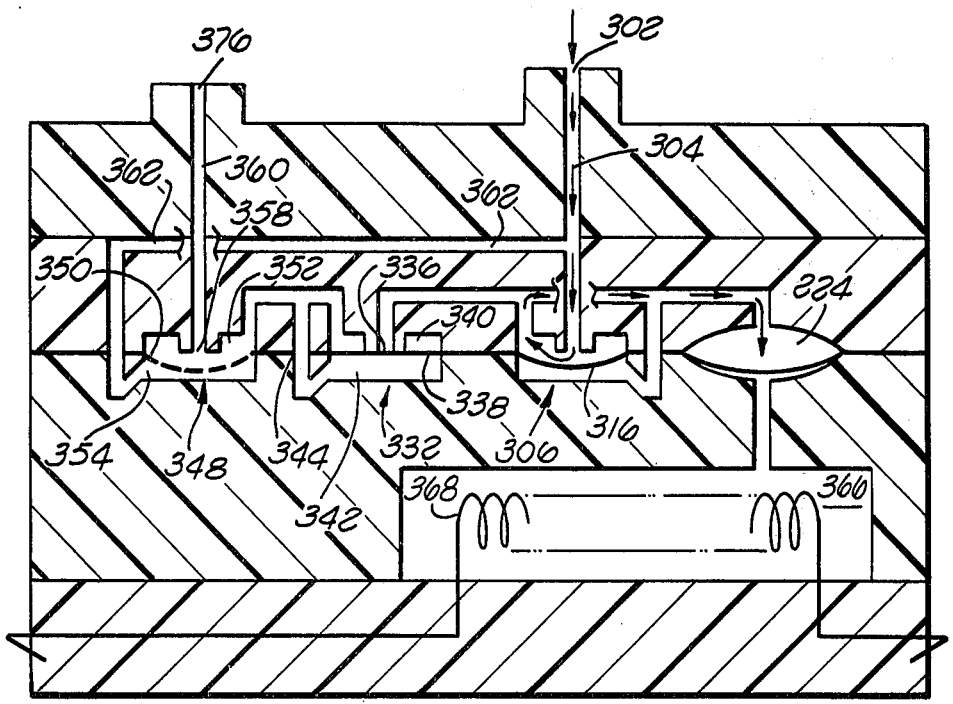

Referring now to FIGS. 3A and 3B, a cross section of the preferred embodiment of the pump apparatus of the invention has a pump chamber 320, an input valve 306, and output valve 332, and a flow-through prevention valve 348. Each of the valves has a valve chamber defining a valve volume therein. A valve boss with a passageway port in its end extends into the valve volume. A valve diaphragm is positioned in the valve volume across the passageway port in the valve boss to bifurcate the valve volume into a fluid flow volume and a fluid pressure volume. Hence, each valve is in a normally closed position with the diaphragm positioned over the passageway port of the valve boss.

More specifically, the input valve 306 has an input valve boss 308 with an input passageway port 310 in its end. The input passageway port 310 is the terminus of an input passageway 304. Pumped fluid enters the input passageway 304 through an input port 302 in the end of an input boss 300.

An input valve diaphragm 316 bifurcates the input valve volume to define a fluid flow volume 312 and a pressure volume 314. A pressure passageway 318 is interconnected between the fluid flow volume 312 and the fluid pressure volume 314 so that the input valve diaphragm 316 will be displaced from its normally closed position over the input passageway port 310 only when there is a pressure differential between the pumped fluid in the input passageway 304 and the pumped fluid pressure in the valve volume.

The pump chamber 320 is also bifurcated as previously discussed by a pumping diaphragm 322 into a first chamber volume 324 and a second chamber volume 326. A flow passageway 330 is then interconnected to provide unobstructed pumped fluid communication between the first chamber volume 324 and the fluid flow volume 312 and the fluid pressure volume 314 of the input valve 306. The flow passageway 330 terminates at a passageway port 336 in the end of a second valve boss 334 which extends into the valve volume of the output valve 332. An output valve diaphragm 338 bifurcates the output valve 332 into a fluid flow volume 340 and a fluid pressure volume 342. The valve diaphragm 338 extends across the passageway port 336 for maintaining the output valve 332 in a normally closed state. A pressure passageway 344 provides pumped fluid communication between the fluid flow volume 340 and the pressure volume 342 so that the valve diaphragm 338 moves away from the passageway port 336 only when a sufficient pressure differential exits between the pumped fluid pressure in the flow passageway 330 and the pumped fluid pressure in the valve volume of the output valve 332.

The flow-through prevention valve 348 similarly has a valve volume bifurcated by a diaphragm 350 which is positioned across a passageway port 358 in the end of a flow-through prevention valve boss 356. The diaphragm 350 bifurcates the valve volume for defining a fluid flow volume 352 and a fluid pressure volume 354. A flow passageway 346 interconnects the fluid flow volume 340 of the output valve 332 with the fluid flow volume 352 of the flow-through prevention valve 348. A pressure passageway 362 interconnects the fluid pressure volume 354 to the input passageway 304.

The passageway port in the flow-through prevention valve boss 356 is the start of an exit passageway 360 which extends through the pump apparatus and has a terminus at an exit port 376 in the end of an exit passageway boss 374.

In order to move the pumped fluid into the pump apparatus, a pumping fluid is provided in a heating chamber 366 interconnected to the second chamber volume 326 by a passageway 364. A heating filament or ribbon 368 is positioned in the heating chamber 366. The heating element or ribbon 368 is electrically coupled to a pair of terminals 370 and 372 to which an electrical power source is attached to provide intermittent electrical pulses to the heating element 368.

In operation, when an electrical pulse is applied to the heating element 368, the pumping fluid in the heating chamber 366 heats causing the pumping diaphragm 322 to be displaced in such a way that the first chamber volume 324 decreases which causes the pumped fluid to be forced out of the first chamber volume 324 along the flow passageway 330 causing the output valve diaphragm 338 to open allowing the pumped fluid to pass through the output valve 332. When the output valve 332 opens, the pumped fluid passes through the flow passageway 346 and exerts pressure against the flow-through prevention valve diaphragm 350 causing it to be displaced downward thus allowing the pumped fluid to flow out the exit passageway 360. As previously described, in this operating state, the input valve in diaphragm 316 remains closed because the pressure in the fluid flow volume 312 and in the pressure volume 314 is equalized by the pressure passageway 318.

Referring now to FIG. 3B, the operation of the pump is illustrated when an electrical pulse is not passing through the heating filament 368 in the heating chamber 366. In this state, the pumping fluid volume decreases causing the pumping diaphragm 322 to move downward towards the heating chamber 366. This movement causes the first chamber volume 324 to increase which causes pumped fluid to be drawn into the first chamber volume 324. As the pumped fluid is drawn into the first chamber volume 324, a suction effect causes the output valve diaphragm 338 of the output valve 332 to be held tightly against the passageway port 336, thus assuring that the output valve 332 will remain closed. At the same time, the suction or negative pressure of the pumped fluid causes a pressure differential between the input passageway 304 and the input valve volume thus causing the diaphragm 316 of the input valve 306 to be displaced downward allowing pumped fluid to flow through the input valve 306 into the first chamber volume 324. If there is no pressure head at either the input port 302 or the exit port 376, then the flow-through prevention valve 348 will remain closed.

It will be appreciated that there may be a positive or negative head pressure at either the input or the exit ports 302 or 376, respectively. For example, a sufficiently large positive head pressure at the exit port 376 can result in the opening of the flow-through prevention valve 348. However, the pressure passageway 344 of the output valve 332 equalizes the pressure volume 342 in the output valve 332 thus preventing displacement of the valve diaphragm 338 to maintain the output valve in a closed state even though the flow-through prevention valve opens in response to a positive head pressure in the exit passageway 360.

On the other hand, if a positive head pressure exists at the input port 302 the input valve 316 will open as will the output valve 332 in a manner previously described. However, the input passageway 304 is interconnected by the passageway 362 to the pressure volume 354 of the flow-through prevention valve 348. Hence, a positive head pressure in the input passageway 304 will be applied in the pressure volume 354 but will not be applied in the flow volume 352. Hence, the flow-through prevention valve diaphragm 350 will be forced tightly against the passageway port 358 to keep the flow-through prevention valve closed.

By way of summary then, if a negative head pressure exists at the input port 302, the flow-through prevention valve 348 opens but the output valve 332 closes to prevent pumped fluid flow through the pump apparatus. When a positive head pressure exists at the input port 302 the flow-through prevention valve 348 closes, also preventing pumped fluid flow-through.

Finally, if a sufficiently high, positive head pressure exists at the exit port 376, then the flow-through prevention valve 348 may open but the output valve 332 will close preventing flow-through.

The present invention, thus, provides an apparatus for pumping precise quantities of fluid from a reservoir to a destination and is particularly applicable in intravenous applications where the rate and quantity of fluids introduced into a patient are critical.

What is claimed is:

1. A pumping apparatus for moving a pumped fluid from a reservoir to a destination in response to variations of the pressure of a pumping fluid comprising:

a pump member means having
   an input port for receiving pumped fluid from the reservoir,
   an exit port for expelling pumped fluid to the destination,
   a pumping chamber,
   an input passageway,
   an exit passageway, and
   a passageway network between the input passageway and the exit passageway;
a diaphragm means bifurcating the pumping chamber for defining a first chamber volume for receiving the pumped fluid and a second chamber volume for receiving the pumping fluid,
variable pressure means for intermittently varying the pressure of the pumping fluid for alternately increasing the second chamber volume to increase the pressure of the pumped fluid and expel it from the first chamber volume and decreasing the second chamber volume to decrease the pressure of the pumped fluid and draw it into the first chamber volume;
first valve means positioned between the input passageway and the passageway network and responsive to the pressure of the pumped fluid in the first chamber volume;
second valve means positioned in the passageway network for being responsive to the pressure of the pumped fluid in the first chamber volume, the first valve means being opened when the second valve means closes and the first valve means being closed when the second valve means opens in response to the variations in pumping fluid pressure;
third valve means coupled between the exit passageway and the second valve means in the passageway network for preventing pumped fluid flow-through the pump in response to a pressure head at the input or exit ports, the third valve means coupled for closing at least one of the first, second, or third valves in response to the head pressure at the input and exit ports.

2. The pumping apparatus of claim 1 wherein each of the first, second and third valve means comprises:
   a valve chamber defining a valve volume therein;
   a valve boss extending into the valve volume having a passageway port in the end thereof; and
   a valve diaphragm bifurcating the valve volume for defining a fluid flow volume and a fluid pressure volume, the valve diaphragm positioned in a normally closed configuration over the passageway port of the valve boss for preventing pumped fluid flow through the passageway port into the fluid flow volume.

3. The pumping apparatus of claim 2 wherein the passageway network further comprises:
   first pressure passageway means interconnecting the fluid pressure volume and the fluid flow volume of the first valve means;
   second pressure passageway means interconnecting the fluid pressure volume and the fluid flow volume of the second valve means;
   third pressure passageway means interconnecting the fluid pressure volume of the third valve means to the input passageway;
   first flow passageway means interconnecting the fluid flow volume of the first valve means and the first chamber volume of the pumping chamber;

second flow passageway means interconnecting the passageway port of the second valve means and the first chamber volume of the pumping chamber; and third flow passageway means interconnecting the fluid flow volumes of the second and third valve means, the passageway port of the third valve means being a terminus of the exit passageway and the passageway port of the first valve means being a terminus of the input passageway.

4. The pumping apparatus of claim 1 or 3 wherein the variable pressure means is responsive to an external source of electrical power, and comprises:

an enclosure means interconnected to the second chamber volume;

a quantity of pumping fluid contained by the enclosure means and the second chamber volume;

a heater means in the enclosure means for being interconnected to the external source of the electrical power, and for intermittently heating the pumping fluid and increasing the volume of the pumping fluid to displace the diaphragm means and increase the second chamber volume.

5. A pumping apparatus for moving a pumped fluid from a reservoir to a destination in response to variation of the pressure of a pumping fluid comprising:

an input port means for receiving pumped fluid from the reservoir;

an exit port means for expelling pumped fluid to the destination;

a pumping chamber means defining a pumping volume having a chamber diaphragm for bifurcating the pumping volume into a first chamber volume for receiving the pumped fluid and a second chamber volume for receiving the pumping fluid, the chamber diaphragm being movable in response to pumping fluid pressure in the second chamber volume;

unidirectional flow control means for transferring pumped fluid through the pumping apparatus in only one direction comprising:

first valve means for controlling the flow of pumped fluid into the pumping assembly in response to movement of the chamber diaphragm, and second valve means for controlling the flow of pumped fluid out from the pumping apparatus in response to the movement of the chamber diaphragm, the first valve means opening and the second valve means closing in response to chamber diaphragm movement in one direction and the first valve means closing and the second valve means opening in response to chamber diaphragm movement in a second direction; and flow-through prevention means for preventing pumped fluid flow through the pumping apparatus in response to a pressure head at the input port means or exit port means of the pumping assembly when the chamber diaphragm is quiescent, comprising:

third valve means interconnected for being closed in response to an input port means head pressure larger than an exit port means head pressure, and further interconnected for closing one of the first or second valve means when the third valve is opened in response to an input port means head pressure less than the exit port means head pressure.

6. The pumping apparatus of claim 5 wherein each of the first, second and third valve means comprises:

a valve chamber means defining a valve volume therein;

a valve boss extending into the valve volume having a passageway port in the end thereof; and a valve diaphragm bifurcating the valve volume for defining a fluid flow volume and a fluid pressure volume, the valve diaphragm positioned in a normally closed configuration over the passageway port of the valve boss for preventing pumped fluid flow-through the passageway port into the fluid flow volume.

7. The pumping apparatus of claim 6 further comprising:

first pressure passageway means interconnecting the fluid pressure volume and the fluid flow volume of the first valve means;

second pressure passageway means interconnecting the fluid pressure volume and the fluid flow volume of the second valve means;

third pressure passageway means interconnecting the fluid pressure volume of the third valve means to the input passageway;

first flow passageway means interconnecting the fluid flow volume of the first valve means and the first chamber volume of the pumping chamber;

second flow passageway means interconnecting the passageway port of the second valve means and the first chamber volume of the pumping chamber; and third flow passageway means interconnecting the fluid flow volume of the second and third valve means, the passageway port of the third valve means being a terminus of the exit passageway and the passageway port of the first valve means being the terminus of the input passageway.

8. The pumping apparatus of claim 5 or 7 operable in response to an external electrical power source further comprising:

variable pressure means responsive to the external electrical power source for causing intermittent pressure variations in the pumping fluid, the variable pressure means comprising:

an enclosure means interconnected to the second chamber volume for confining the pumping fluid, an electrical heater means in the enclosure for being interconnected to the external electrical power source and intermittently heating the pumping fluid and increasing the volume of the pumping fluid to displace the chamber diaphragm to increase the second chamber volume.

* * * * *